(12) United States Patent
Matsumura et al.

(10) Patent No.: US 10,098,552 B2
(45) Date of Patent: Oct. 16, 2018

(54) BLOOD PRESSURE MEASUREMENT DEVICE

(71) Applicants: Naomi Matsumura, Osaka (JP); Yukiya Sawanoi, Nara (JP); Tsuyoshi Kitagawa, Kyoto (JP); Shota Umeda, Shiga (JP)

(72) Inventors: Naomi Matsumura, Osaka (JP); Yukiya Sawanoi, Nara (JP); Tsuyoshi Kitagawa, Kyoto (JP); Shota Umeda, Shiga (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 1310 days.

(21) Appl. No.: 13/749,210

(22) Filed: Jan. 24, 2013

(65) Prior Publication Data

US 2013/0190576 A1    Jul. 25, 2013

(30) Foreign Application Priority Data

Jan. 25, 2012  (JP) ................................. 2012-012736

(51) Int. Cl.
*A61B 5/022* (2006.01)
*A61B 5/024* (2006.01)
*A61B 5/0235* (2006.01)
*A61B 5/0225* (2006.01)

(52) U.S. Cl.
CPC .............. *A61B 5/022* (2013.01); *A61B 5/024* (2013.01); *A61B 5/0235* (2013.01); *A61B 5/0225* (2013.01); *A61B 5/02225* (2013.01); *A61B 5/02233* (2013.01); *A61B 5/02422* (2013.01)

(58) Field of Classification Search
None
See application file for complete search history.

(56) References Cited

U.S. PATENT DOCUMENTS

| 4,378,807 | A | * | 4/1983 | Peterson | ............ A61B 5/02141 |
| | | | | | 128/900 |
| 5,139,026 | A | * | 8/1992 | Niwa | ..................... A61B 5/021 |
| | | | | | 600/485 |
| 2004/0024325 | A1 | * | 2/2004 | Nishibayashi | ..... A61B 5/02225 |
| | | | | | 600/492 |
| 2008/0183084 | A1 | * | 7/2008 | Tseng | ..................... A61B 5/022 |
| | | | | | 600/485 |

(Continued)

*Primary Examiner* — Jacqueline Cheng
*Assistant Examiner* — Jairo Portillo
(74) *Attorney, Agent, or Firm* — Osha Liang LLP

(57) ABSTRACT

A blood pressure and pulse measurement device includes a cuff including a first air bladder, a pressure sensor, a pressing member, a pulse wave sensor, and an operation unit. When measurement of the blood pressure is instructed by the operation unit, the first air bladder of the cuff is inflated to increase inner pressure to a sufficient level such that the blood pressure of the patient can be measured by the pressure sensor and then deflated. When measurement of the blood pressure is not instructed by the operation unit, air of the first air bladder of the cuff is released such that the measurement location of the patient is not substantially pressed by the first air bladder, and the measurement location of the patient is pressed by the pressing member with sufficient pressure such that pulse of the patient can be detected by the pulse wave sensor.

19 Claims, 17 Drawing Sheets

(56) References Cited

U.S. PATENT DOCUMENTS

2010/0076328 A1* 3/2010 Matsumura ............ A61B 5/021
    600/500
2010/0292587 A1* 11/2010 Inoue ................ A61B 5/02141
    600/499
2010/0324430 A1* 12/2010 Inoue ................ A61B 5/02116
    600/493
2010/0331709 A1* 12/2010 Matsumura ........ A61B 5/02422
    600/490

* cited by examiner

BLOOD PRESSURE MEASUREMENT DEVICE

BACKGROUND OF THE INVENTION

1. Field of the Invention

This invention relates to a measurement device and a measuring method, more particularly to a measurement device that uses a cuff to measure blood pressure.

2. Description of the Related Art

Based on the nature of a disease, there are cases where it is necessary to capture blood pressure variations of a long period of time, for example, of a circadian pattern and the like. In order to know blood pressure variations, a way of use is known where a measurement device is mounted and blood pressure measurements are performed at predetermined intervals over a long period. Further, there is also a need of desiring to also capture, along with a blood pressure value in the period of time, a variation in pulse in that period of time.

As a sphygmomanometer used to measure blood pressure variations in a long period of time, a wrist sphygmomanometer where a cuff is mounted on a wrist can reduce a burden on a patient over a type where the cuff is mounted on an upper arm. Furthermore, a wrist radial artery can be said to be a suitable area for pulse measurement because the artery is located in a place where a subcutaneous is shallower than the upper arm.

Then, using a wrist sphygmomanometer mounting a function to measure pulse as a device to measure blood pressure and pulse over a long period of time, it can be envisioned that the wrist sphygmomanometer measures pulse in a time period other than at the time of measuring blood pressure.

Here, a method of measuring pulse rate is known where a volume change of an artery in a location where the subcutaneous is relatively shallow is noninvasively detected as a method for measuring pulse. In particular, as measurement methods of simple configuration there are, 1) A method using a cuff that mildly compresses a wrist of the patient and detects variations in cuff pressure with a pressure sensor, and 2) A method that measures the volume change of the artery using a photoelectronic sensor or an impedance sensor mounted and arranged above the artery.

Whether in the case of measuring with the method of 1) or in the case of measuring with the method of 2) above, because a cuff is provided in the sphygmomanometer, use of the cuff is possible. That is, it can be envisioned that the cuff is used for the mild compression of the methods of 1) and 2) above and for attaching the sensors to skin of the method of 2).

Incidentally, the cuff used for blood pressure measurement is configured of an effective size to wrap around a measurement location in a circumferential direction. This size is regulated through, for example, the American Heart Association (AHA) and the like. When attempting to measure continuous pulse on timing other than at the time of measuring blood pressure using this kind of cuff, it is necessary to keep lightly compressing on the wrist of the patient over a long period of time with either the method of 1) or the method of 2) above. Because of that, a possibility increases that a venous flow of an entire circumference of the wrist will be blocked and blood stasis will occur. Also, by compressing the entire circumference of the wrist over a long period of time, the patient may be caused to feel a sense of restraint.

SUMMARY OF THE INVENTION

Accordingly, one or more embodiments of the present invention provide a measurement device that suppresses the occurrence of blood stasis, and also suppresses the burden on the patient and can, along with blood pressure measurement, accurately provide continuous measurement of pulse other than at the time of measuring blood pressure.

One or more embodiments of the present invention relate to a blood pressure and pulse measurement device that comprises a cuff including a first air bladder for wrapping around a measurement location of a patient; a pressure sensor connected to the cuff for measuring an inner pressure of the first air bladder; a pressing member mounted on a portion of an inner face of the first air bladder which contacts the measurement location of the patient when the cuff is wrapped therearound; a pulse wave sensor mounted on the pressing member for detecting pulse of the patient; and an operation unit for instructing the device to measure a blood pressure and pulse. When measurement of the blood pressure is instructed by the operation unit, the first air bladder of the cuff is inflated to increase inner pressure to a sufficient level such that the blood pressure of the patient can be measured by the pressure sensor and then deflated. When measurement of the blood pressure is not instructed by the operation unit, air of the first air bladder of the cuff is released such that the measurement location of the patient is not substantially pressed by the first air bladder, and the measurement location of the patient is pressed by the pressing member with sufficient pressure such that pulse of the patient can be detected by the pulse wave sensor at the position where the measurement location of the patient is contacted by the pulse wave sensor.

According to one or more embodiments of the present invention, the pulse wave sensor is mounted on the pressing member at a position where the pressing member contacts the measurement location.

According to one or more embodiments of the present invention, the pressing member is constituted such that the pulse wave sensor is positioned above the artery of the patient.

According to one or more embodiments of the present invention, the pressing member comprises a second air bladder, and at the time of measuring blood pressure, air of the second air bladder is released such that the measurement location of the patient is substantially pressed only by the first air bladder.

According to one or more embodiments of the present invention, the pulse wave sensor is a photoelectronic sensor According to one or more embodiments of the present invention, the pulse wave sensor is an impedance sensor.

According to one or more embodiments of the present invention, the cuff and the pressing member is constituted such that they can be mounted on a wrist of the patient.

According to one or more embodiments of the present invention, measurement of blood pressure is instructed by the operation unit at a predetermined interval.

According to one or more embodiments of the present invention, detection of pulse of the patient is suspended when the first air bladder is inflated and/or deflated for measurement of blood pressure.

One or more embodiments of the present invention relate to a cuff of blood pressure and pulse measurement device comprising: a first air bladder for wrapping around a measurement location of the patient; a pressure sensor connected to the first air bladder for measuring an inner pressure of the first air bladder; a pressing member mounted on a portion of an inner face of the air bladder which contacts the measurement location of the patient when the cuff is wrapped therearound; a pulse wave sensor mounted on the pressing member for detecting pulse of the patient; and an operation unit provided in the blood pressure measurement device and connected to the cuff for instructing the device to measure a blood pressure and pulse of the patient. When measurement of the blood pressure is instructed by the operation unit, the first air bladder of the cuff is inflated to increase inner pressure to a sufficient level such that the blood pressure of the patient can be measured by the pressure sensor and then deflated. When measurement of the blood pressure is not instructed by the operation unit, air of the first air bladder of the cuff is released such that the measurement location of the patient is not substantially pressed by the cuff, and the measurement location of the patient is pressed by the pressing member with sufficient pressure such that pulse of the patient can be detected by the pulse wave sensor at the position where the measurement location of the patient is contacted by the pulse wave sensor.

One or more embodiments of the present invention relate to a method for measuring blood pressure and pulse of a patient comprising: wrapping a cuff comprising a first air bladder and a pressure sensor around a measurement location of the patient, wherein the cuff is provided with a pressing member mounted on a portion of an inner face of the first air bladder and a pulse wave sensor mounted on the pressing member; inflating the first air bladder of the cuff to a sufficient inner pressure level such that blood pressure of the patient can be detect by the pressure sensor and then deflated, and releasing air of the first air bladder of the cuff such that measurement location of the patient is not substantially pressed by the air bladder, and the measurement location is pressed by the pressing member with sufficient pressure such that pulse of the patient can be detected by the pulse wave sensor at the position where the pulse wave sensor contacts the measurement location of the patient.

According to one or more embodiments of the present invention, blood pressure and pulse of a patient can be accurately measured in a long period of time while suppressing burden of the patient.

DETAILED DESCRIPTION OF INVENTION

A description will be given hereinafter with reference to drawings of an embodiment of the present invention. In the following description, the same reference numbers will be assigned to the same components and compositional elements. The names and functions of these are also the same.

<Device Configuration>

Figure 1:
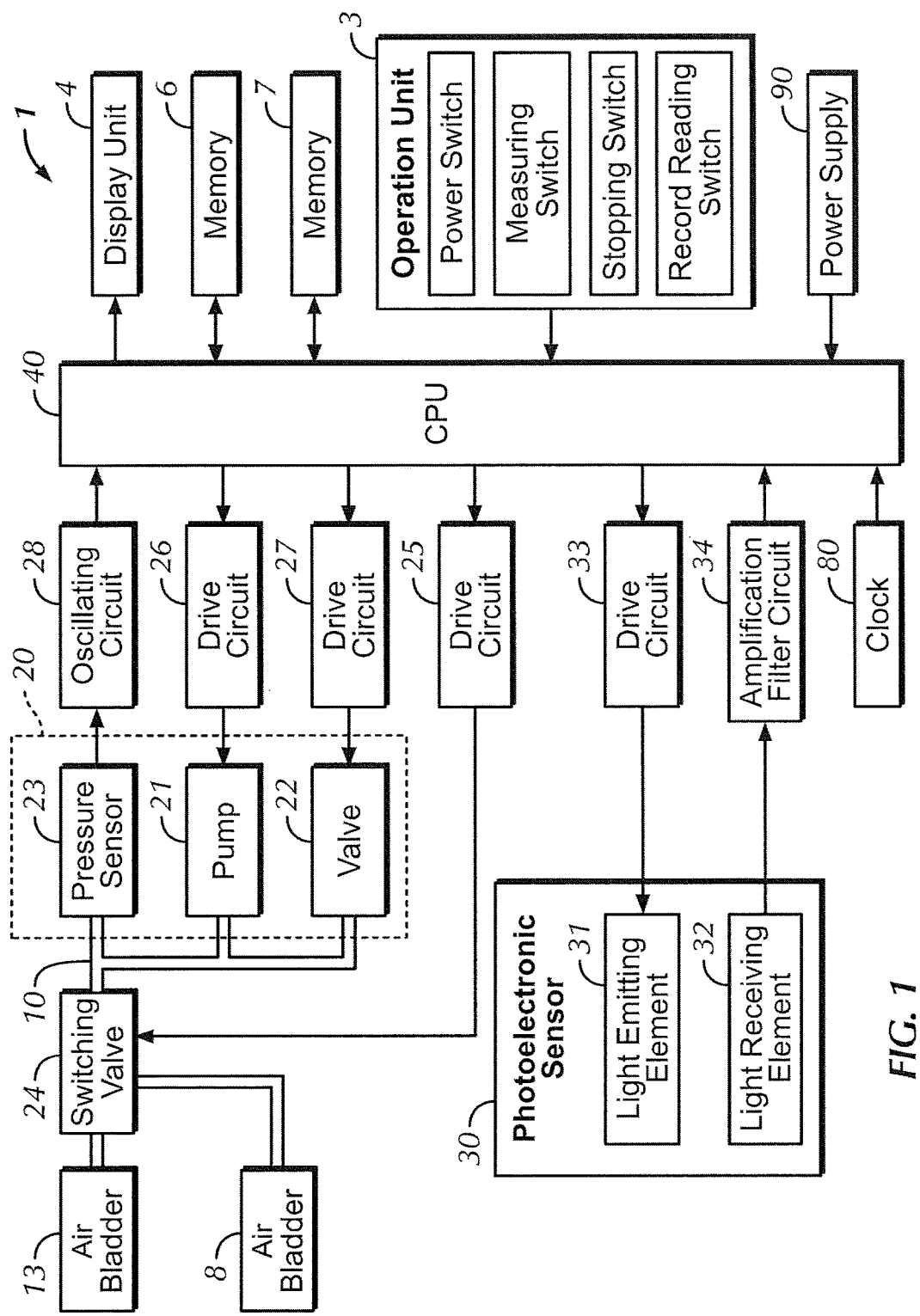
FIG. 1 is a block diagram illustrating a specific example of a device configuration of an electronic sphygmomanometer (herein after a sphygmomanometer) as a measurement device that relates to an embodiment.

FIG. 1 is a block diagram illustrating a specific example of a device configuration of an electronic sphygmomanometer (herein after a sphygmomanometer) 1 as a measurement device that relates to an embodiment. The sphygmomanometer 1 is used to measure blood pressure variation in a long period of time. Because of that, a wrist sphygmomanometer attaching a cuff (air bladder) to a wrist, as mentioned above, is assumed. However, this is not limited to only a wrist, but application is also possible of attachment to locations of other limbs of an upper arm or an ankle and the like.

With reference to FIG. 1, the sphygmomanometer 1 connects these air bladders, including an air bladder for measuring 13 and an air bladder for light compression 8, to an air system 20 by an air pipe 10 through a switching valve 24. A pressure sensor 23 for measuring the inner pressure of air bladders 8 and 13, a pump 21 for performing inflation/deflation of air bladders 8 and 13 and a valve 22 are included in the air system 20.

The pressure sensor 23, the pump 21 and the valve 22 are each electrically connected to an oscillating circuit 28, a drive circuit 26, and a drive circuit 27. The oscillating circuit 28, the drive circuit 26 and, additionally, the drive circuit 27 are all electrically connected to the Central Processing Unit (CPU) 40 that controls the entire sphygmomanometer 1. The switching valve 24 is electrically connected to a drive circuit 25 and, additionally, the drive circuit 25 is electrically connected to a CPU 40.

Additionally, a display unit 4; an operation unit 3; a memory 6 for processing that stores a program executed by the CPU 40 and becomes an operation region at the time the program is executed; a memory 7 for data storage for storing required information and the like for measurement results, control, and calculation; a clock 80; and a power supply 90 are connected to the CPU 40.

The switching valve 24, as one example, corresponds to a 3-port valve comprising the three values of an air bladder 8 valve, an air bladder 13 valve and an air system 20 valve that is driven to open and close the air bladder 8 valve and the air bladder 13 valve by the drive circuit 25 that follows control signals from the CPU 40. That is, a state of the air bladder 8 being connected to the air system 20 by the air pipe 10 and a state of the air bladder 13 being connected to the air system 20 by the air pipe 10 are switched following a control signal from the CPU 40.

The drive circuit 26 drives the pump 21 following the control signal from the CPU 40. By so doing, air is infused into air bladder 8 and also air bladder 13.

The drive circuit 27 drives the valve 22 by following each control signal from the CPU 40. Through this, the valve 22 is opened and closed.

The pressure sensor 23 is a capacitance-type pressure sensor in which the capacitance value changes depending on the change in pressure within the air bladders 8 and 13. The pressure sensor 23 is connected to the oscillating circuit 28 and the oscillating circuit 28 converts to a signal with an oscillating frequency according to the capacitance value of the pressure sensor 23 and is input into the CPU 40.

Note that, in this example the air bladder for measuring 13 and the air bladder for light compression 8 are both configured to be connected to the air system 20 across switching valve 24, but the air bladder for measuring 13 and the air bladder for light compression 8 may also be in a configuration where each is connected to a different air system with separate inner pressure control.

Additionally, with reference to FIG. 1, the sphygmomanometer 1 includes a photoelectronic sensor 30 having a light emitting element 31 and a light receiving element 32 as a pulse wave sensor for detecting a pulse wave. The light emitting element 31 irradiates the artery with light, and the light receiving element 32 receives the light transmitted through the artery. The light emitting element 31 uses an element that emits light of a high wavelength region near 940 nm, which is a wavelength that easily transmits through body tissue. The light receiving element 32 also uses an element that receives light of a high wavelength region near 940 nm.

The light emitting element 31 is electrically connected to a drive circuit 33 and, additionally, the drive circuit 33 is electrically connected to the CPU 40. The drive circuit 33 causes the light emitting element 31 to emit light and quench light following the control signal from the CPU 40.

The light receiving element 32 is electrically connected to an amplification filter circuit 34 and, additionally, the amplification filter circuit 34 is electrically connected to the CPU 40. The light receiving element 32 outputs a sensor signal according to the amount of received light to the amplification filter circuit 34, and the amplification filter circuit 34 amplifies the signal a predetermined proportion and outputs the signal to the CPU 40.

The air bladder 8 is used to attach the photoelectronic sensor 30 to the skin and to lightly compress the artery.

Figure 2:
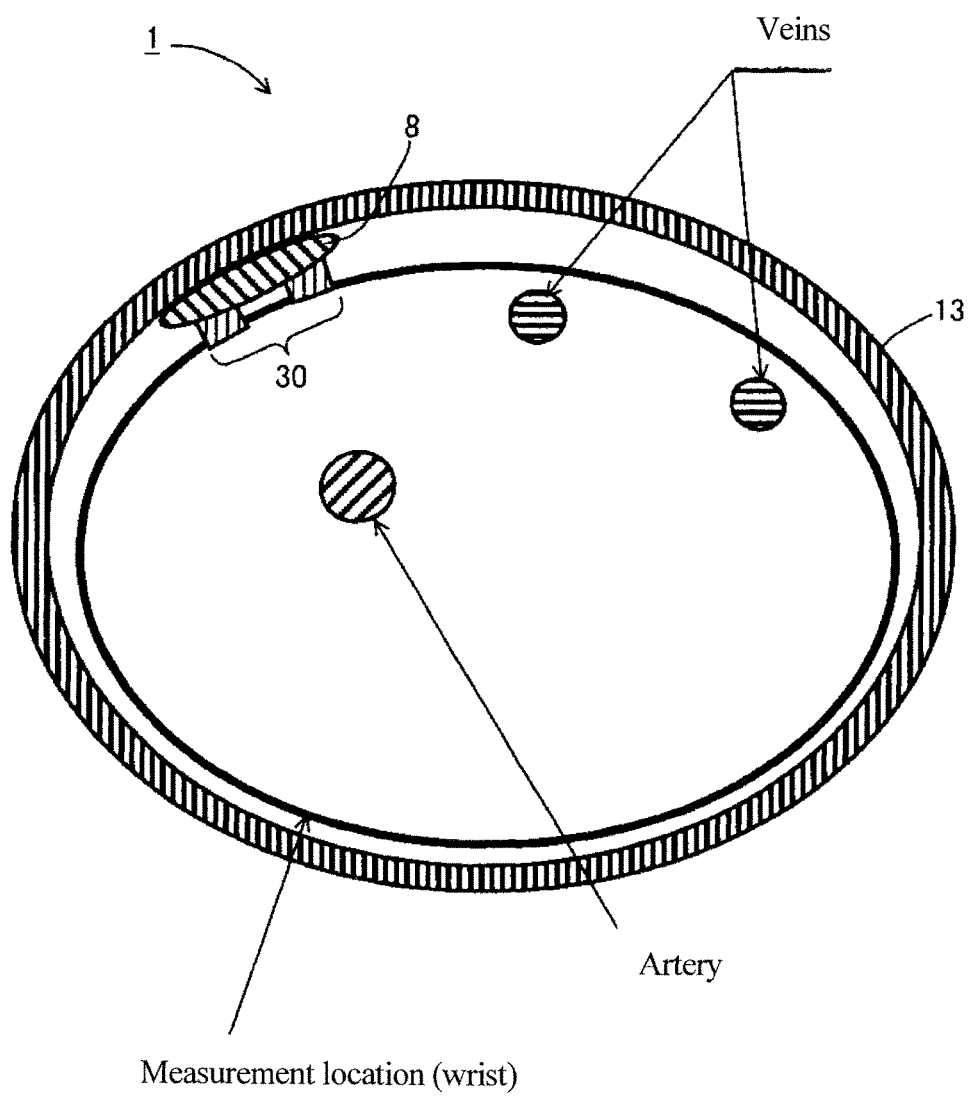
FIG. 2 is a schematic indicating a cross section of the attachment portion in a mounted state of a sphygmomanometer to a wrist that is a measurement location.

FIG. 2 is a schematic indicating a cross section of the mounted portion of a mounted state of the sphygmomanometer 1 to a wrist that is a measurement location.

With reference to FIG. 2, the photoelectronic sensor 30 is provided on one side of the air bladder for light compression 8 as a light source direction on an opposite side to the air bladder 8. Then, the sphygmomanometer 1 is mounted so that the photoelectronic sensor 30 is above the wrist radial artery. By mounting in this way, the photoelectronic sensor 30 is pressed in above the wrist radial artery by the air bladder for light compression 8.

It is enough if the air bladder 8 is of a size to cover all of the photoelectronic sensor 30 and press in above the wrist radial artery, for example, a size where the length of a circumferential direction (wrist circumferential direction) is about 15 mm and a length in a perpendicular direction to that (wrist lengthwise direction) is about 30 mm.

Additionally, with reference to FIG. 2, the air bladder for measuring 13 contacts a surface of a side opposite to a surface of a side where the photoelectronic sensor 30 of the air bladder for light compression 8 is provided and, at the least covers all of the air bladder 8. Then, the sphygmomanometer 1 is mounted by wrapping the air bladder 13 around the wrist with the air bladder for light compression 8 as the wrist side, which is the measurement location.

It is enough if the air bladder 13 is at the least of a size larger than the air bladder for light compression 8 and to cover all of a cuff for light compression and to wrap around the wrist, for example, a size where the length of a circumferential direction (wrist circumferential direction) is about 150 mm and a length in a perpendicular direction to that (wrist lengthwise direction) is about 45 mm.

<Operation Overview>

A blood pressure measurement operation is performed by the sphygmomanometer 1 at prescribed timing of a predetermined time interval and the like and when blood pressure measurement is instructed. Also, when blood pressure measurement is not being performed, a pulse measurement operation is performed.

Figure 3:
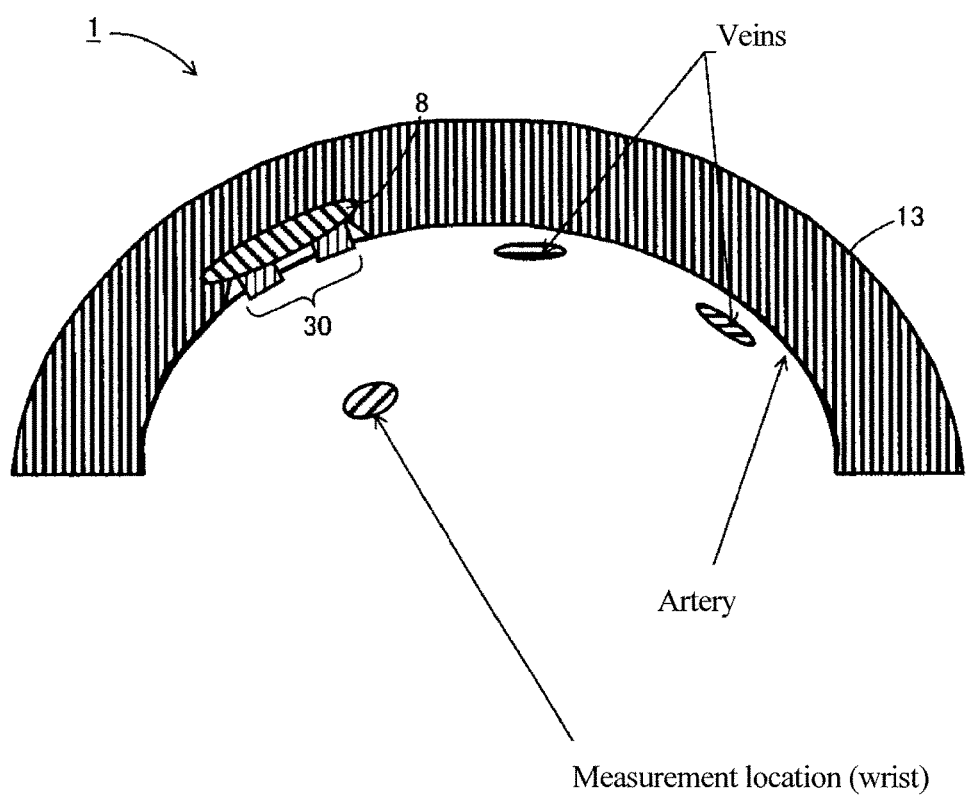
FIG. 3 is a diagram indicating the manner of an air bladder for a pressure gauge at the time of measuring blood pressure and an air bladder for measurement.
Figure 4:
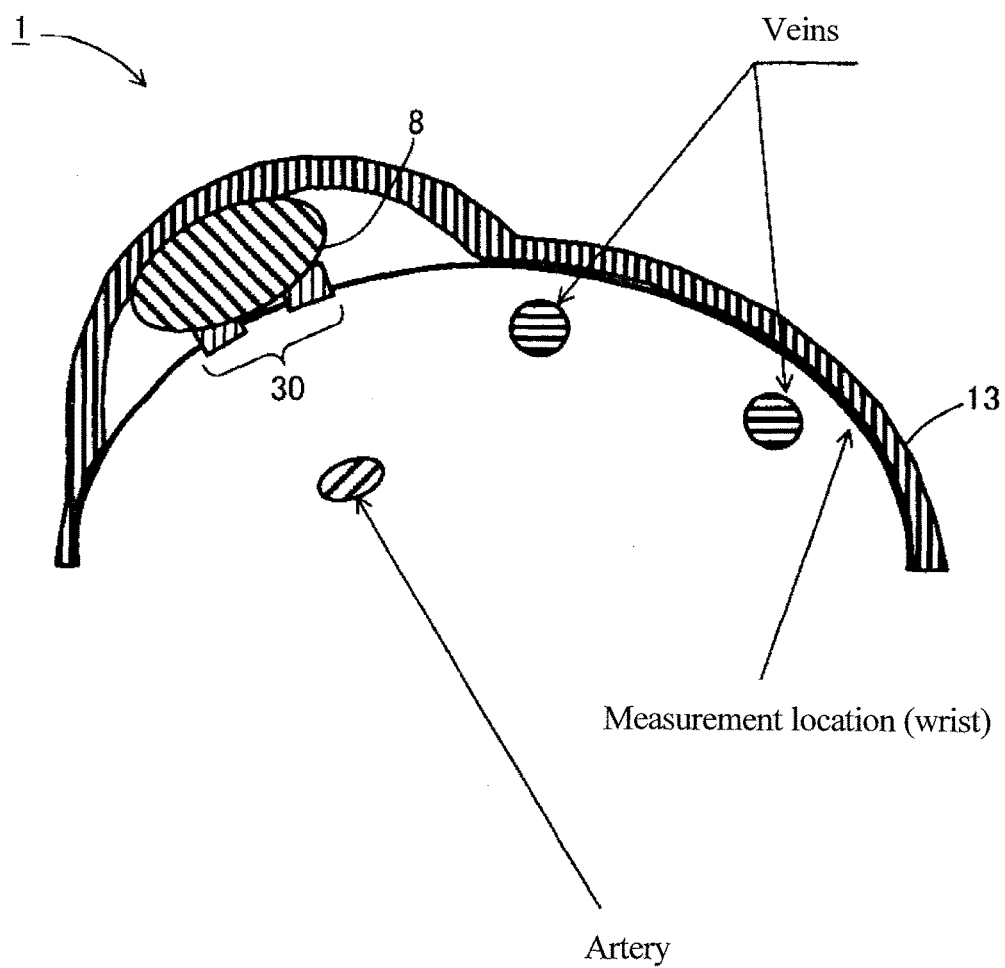
FIG. 4 is a diagram indicating the manner of an air bladder for a pressure gauge at the time of measuring pulse and an air bladder for measurement.

FIG. 3 and FIG. 4 are diagrams indicating the manner of air bladders 8 and 13 at the time of measuring operation. FIG. 3 indicates the manner of air bladders 8 and 13 at the time of measuring blood pressure, and FIG. 4 indicates the manner of air bladders 8 and 13 at the time of measuring pulse.

With reference to FIG. 3, at the time of measuring blood pressure, only the air bladder for measuring 13 pressurizes, the air bladder for light compression 8 does not pressurize.

With reference to FIG. 4, at the time of measuring pulse, only the air bladder for light compression 8 pressurizes; the air bladder for measuring 13 does not pressurize.

Because of this, some burden on a patient occurs at the time of measuring blood pressure because the wrist, which is the measurement location, is compressed by the air bladder for measuring 13 that has a larger air capacity than the air bladder for light compression 8, however, this completes in a short period of time and, at the time of measuring pulse, compression by the air bladder for measuring 13 is eliminated and compression is only through the air bladder for light compression 8 that has a smaller air capacity.

<Functional Configuration>

Figure 5:
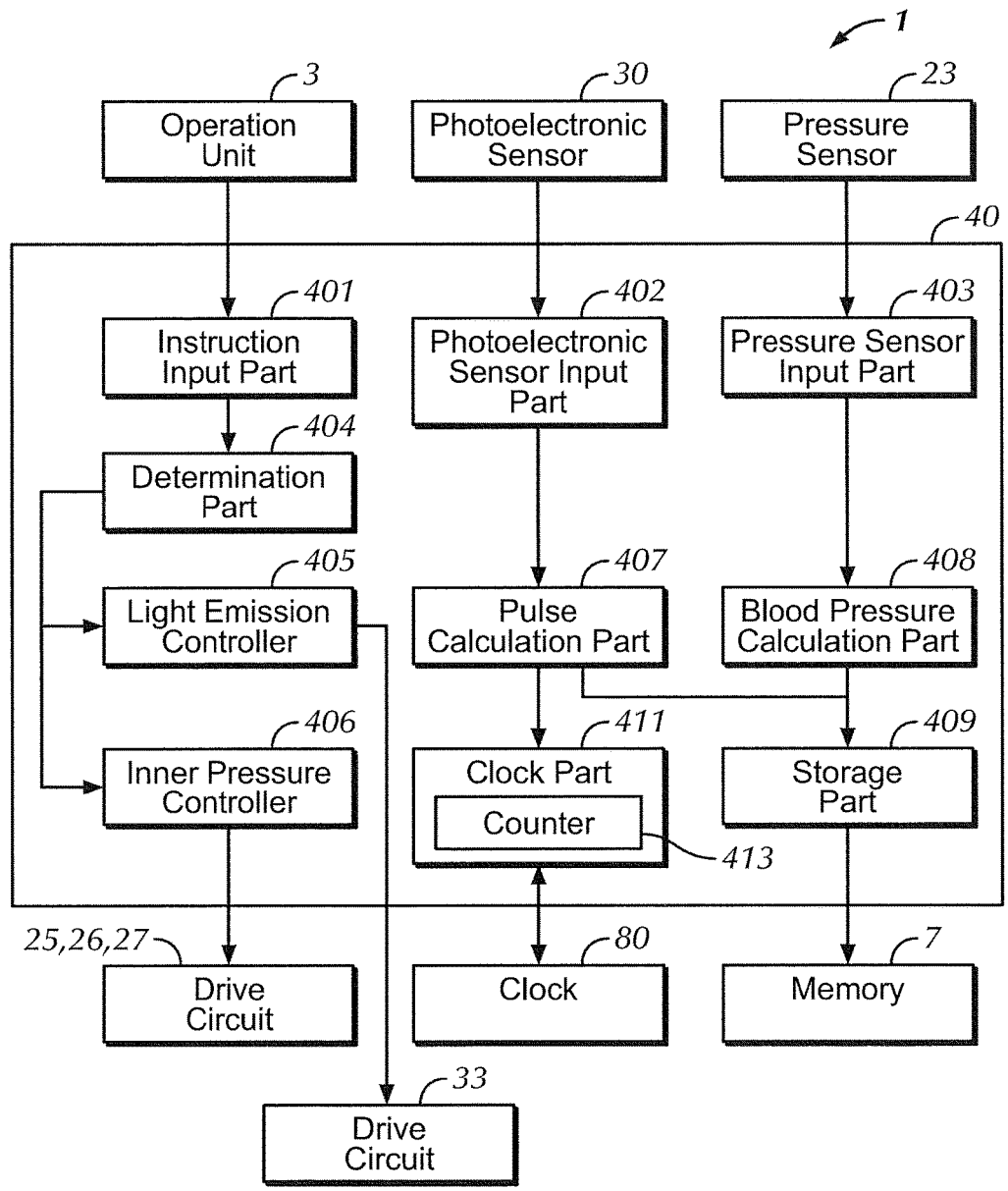
FIG. 5 is a block diagram illustrating a specific example of a functional configuration of a sphygmomanometer.

FIG. 5 is a block diagram illustrating a specific example of a functional configuration of the sphygmomanometer 1 for performing blood pressure measurement and pulse measurement. Each function illustrated in FIG. 5 is formed in the CPU 40 and executed by the CPU 40 by retrieving a program stored in the memory 6, but at least one portion may be implemented through a hardware configuration of a device configuration and an electric circuit and the like illustrated in FIG. 1.

With reference to FIG. 5, the CPU 40 includes an instruction input part 401 for receiving instruction input from the operation unit 3, a photoelectronic sensor input part 402 for receiving input of a sensor signal from the light receiving element 32 of the photoelectronic sensor 30 according to a volume of received light, a pressure sensor input part 403 for receiving input of a sensor signal from the pressure sensor 23 according to an inner pressure of the air bladder 13, a determination part 404 for determining whether to perform the blood pressure measurement operation or the pulse measurement operation according to the instruction input, a light emission controller 405 for controlling light emitting and light quenching of the light emitting element 31 of the photoelectronic sensor 30 in the case of performing the pulse measurement, an inner pressure controller 406 for controlling the inner pressure of air bladders 8 and 13 in the case of performance of the blood pressure measurement and the pulse measurement, a pulse calculation part 407 for calculating pulse based on the sensor signal from the photoelectronic sensor 30, a blood pressure calculation part 408 for calculating a blood pressure value based on the sensor signal from the pressure sensor 23, a storage part 409 for storing calculated results in a prescribed area of the memory 7 and a clock part 411 including a counter 413 for measuring an elapsed time from the completion of the pulse measurement operation.

<Operation Flow>

Figure 6:
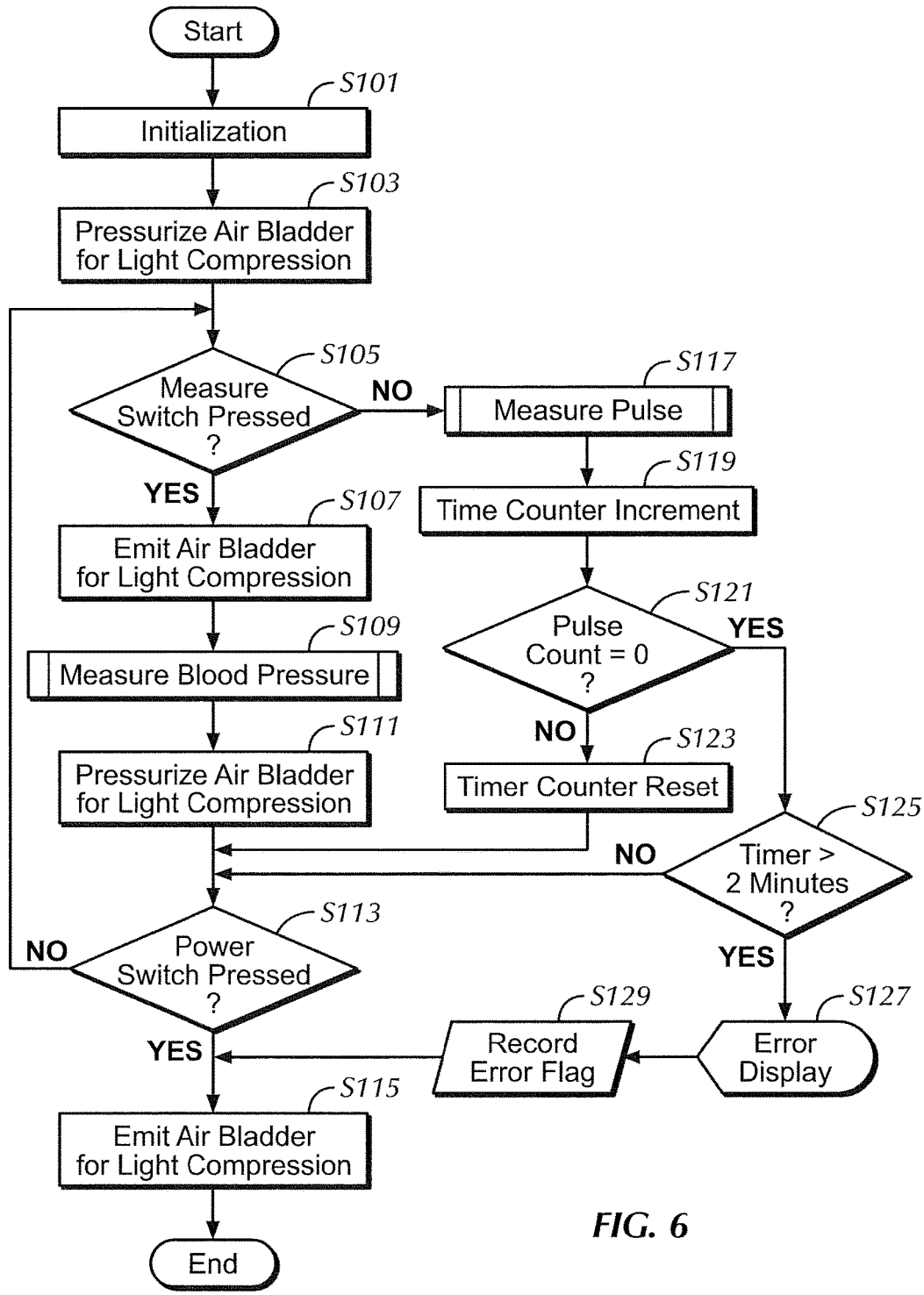
FIG. 6 is a flowchart indicating the flow of a measurement operation with the sphygmomanometer.

FIG. 6 is a flowchart indicating the flow of the measurement operation with the sphygmomanometer 1. The operation illustrated in the flow chart in FIG. 6 is an operation that starts when a power switch included in an operation unit 3 is pressed powering on the sphygmomanometer 1, and is implemented through the CPU 40 executing retrieval of the program stored in the memory 6 and demonstrating each function illustrated in FIG. 5.

With reference to FIG. 6, at step S101, when the sphygmomanometer 1 is powered on, as an initialization process, the CPU 40 initializes a memory area for processing, emits the air inside the air bladder for measuring 13 and the air bladder for light compression 8 and performs 0 mmHg calibration of the pressure sensor.

After initialization is complete, at step S103, the CPU 40 switches the switching valve 24 and upon connecting the air bladder for light compression 8 to the air system 20, closes the valve 22 and drives the pump 21 to pressurize the pressure of the air bladder for light compression 8 to a prescribed pressure. When the inner pressure of the air bladder 8 reaches an already predetermined prescribed pressure, the driving of the pump is stopped and pressurization stops. Here, the prescribed pressure is already predetermined and refers to a pressure recorded in the memory 7 (for example, 30 mmHg). Through this, the inner pressure of the air bladder 8 is maintained at the above already predetermined prescribed pressure.

The CPU 40 monitors whether or not a measuring switch that instructs the start of blood pressure measurement has been pressed. In the case that the measuring switch has been pressed (YES at step S105), the CPU 40 determines a case of blood pressure measurement operation and performs the operation for blood pressure measurement.

That is, at step S107, the CPU 40 completely opens the valve 22. By doing so, the air inside the air bladder for light compression 8 is emitted. After emission, the blood pressure measurement operation is performed at step S109. Here, the blood pressure measurement operation may be a normal blood pressure measurement operation. As one example, a method is utilized where the air bladder for measuring 13 is pressurized and depressurized and systolic blood pressure and diastolic blood pressure are calculated through the Oscillometric method using those changes in inner pressure.

Figure 7:
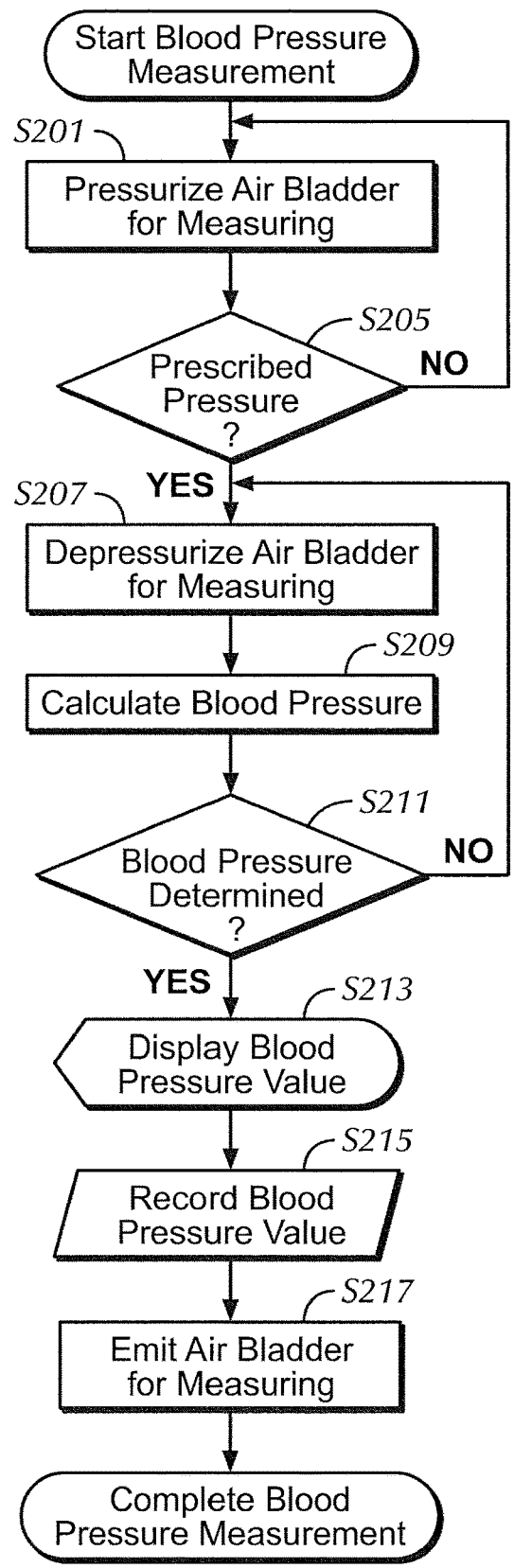
FIG. 7 is a flowchart indicating the flow of a blood pressure measurement operation of S109 of FIG. 6.

With respect to FIG. 7 about specific operation in this case, at step S201, the CPU 40 switches switching valve 24 and closes the valve 22 upon connecting the air bladder for measuring 13 to the air system and drives the pump 21 at a prescribed amount of driving. By doing so, the air bladder for measuring 13 is gradually pressurized.

When cuff pressure reaches a prescribed pressure (YES at step S205), the CPU_40, at step S207, stops the driving of the pump 21 and gradually opens the valve 22. By doing so, the inner pressure of the air bladder 13 is gradually depressurized. Here, the prescribed pressure is a pressure sufficiently higher than the systolic blood pressure (for example, systolic blood pressure+30 mmHg) and is either already recorded in memory 7 or is determined by estimating systolic blood pressure during pressurization.

At step S209, the CPU 40, while gradually depressurizing the air bladder 13, extracts the pressure variations (pressure pulse wave) in conjunction with artery volume changes superimposed on the air bladder 13, applies a prescribed algorithm in the pressure pulse wave signal, and calculates blood pressure. This method can use a conventional Oscillometric method.

Figure 9:
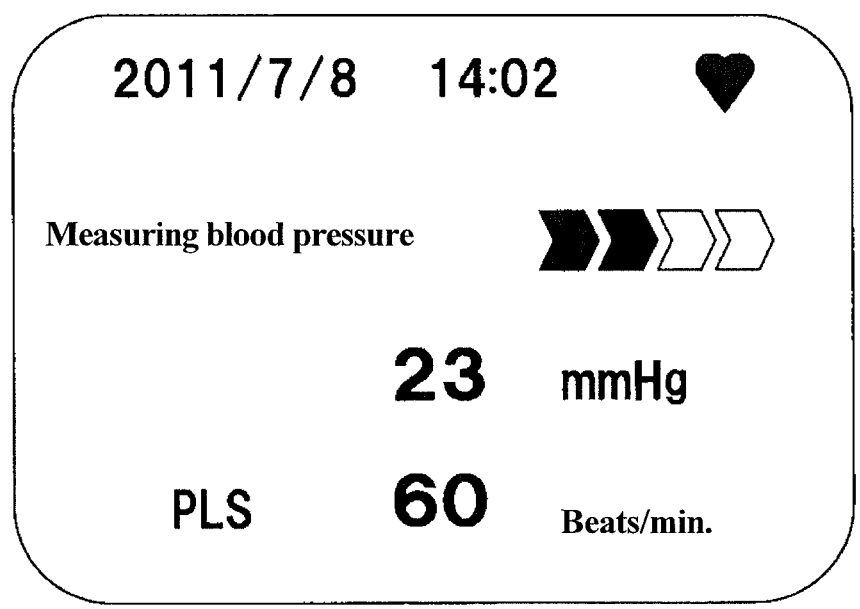
FIG. 9 is a diagram illustrating a specific example of a display screen during the blood pressure measurement operation.

Note that, during the time the above blood pressure measurement operation is being performed, according to one or more embodiments of the present invention, the CPU 40 displays a screen on display unit 4, such as that illustrated in FIG. 9. By doing so in this way, the patient and a person measuring can see that the sphygmomanometer 1 is in the blood pressure measurement operation. Note that, at this time, as illustrated in FIG. 9, the measured pulse may also be displayed together during the blood pressure measurement operation.

Figure 10:
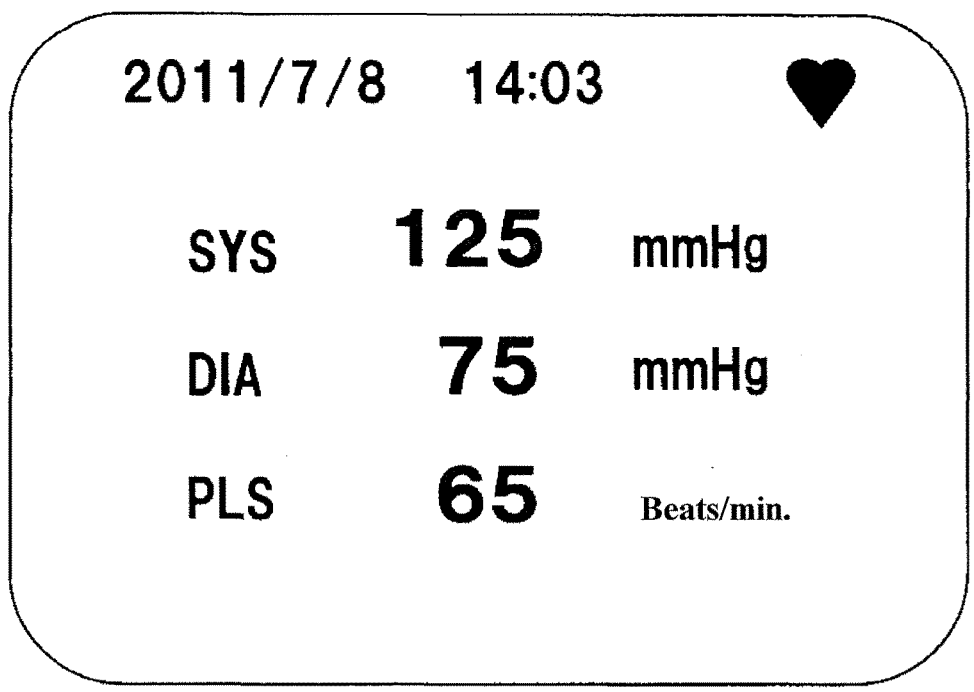
FIG. 10 is a diagram illustrating a specific example of a display screen after the blood pressure measurement operation.

After blood pressure is calculated, when blood pressure value is determined (YES at step S211), the CPU 40, at step S213, displays a screen on display unit 4 that indicates measurement results like those of FIG. 10 and, at step S215, saves measurement results in a prescribed area of the memory 7 (ST209). Note that, at this time, as illustrated in FIG. 10, the measured pulse may also be displayed together during the blood pressure measurement operation.

After that, at step S217, the CPU 40 completely opens the valve 22. By doing so, the air inside the air bladder for measuring 13 is emitted.

Return to FIG. 6 when the above blood pressure measurement operation is complete and the CPU 40, at step S111, performs that same operation as at step S103 above and once again pressurizes the air bladder for light compression 8.

On the other hand, in the case that the measuring switch that instructs the start of blood pressure measurement is not pressed (NO at step 105), the CPU 40 does not perform the blood pressure measurement operation. At this time, the CPU 40 performs the pulse measurement operation [step S117].

Figure 8:
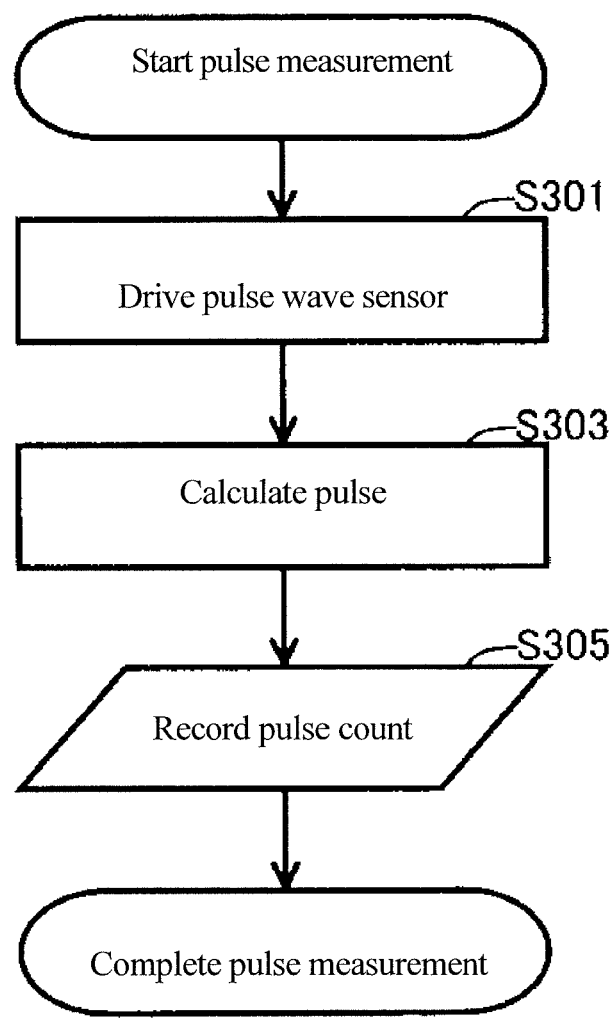
FIG. 8 is a flowchart indicating the flow of a pulse measurement operation of S117 of FIG. 6.

Refer to FIG. 8 about the pulse measurement operation at step S117, the CPU 40, at step S301, causes the light emitting element 31 of the photoelectronic sensor 30 to emit light for a prescribed time period and receives a sensor signal according to the amount of received light from the light receiving element 32. After emitting light for a prescribed time period, the CPU 40 quenches the light emitting element 31. Then, at step S303, the CPU 40 calculates the pulse by applying a prescribed algorithm to the sensor signal.

At step S305, the CPU 40 saves the calculated pulse in a prescribed area of the memory 7. Return to FIG. 6 when the above pulse measurement operation is complete and the CPU 40, at step S119, starts the measurement of the elapsed time from the completion of the pulse measurement operation. In the case that pulse rate is calculated through the pulse measurement operation at step S117 above (NO at step S121), the CPU 40, at step S123, resets the counter of the elapsed time from the completion of the pulse measurement operation and repeats the above operation until the power switch is pressed (NO at step S113).

In the case that pulse rate is not calculated through the pulse measurement operation of step S117 when the count of the continued measurement of elapsed time is 2 minutes or less (NO at step S125), the measurement of elapsed time continues and the aforementioned operation is repeated until the power switch is pressed (NO at step S113).

Figure 11:
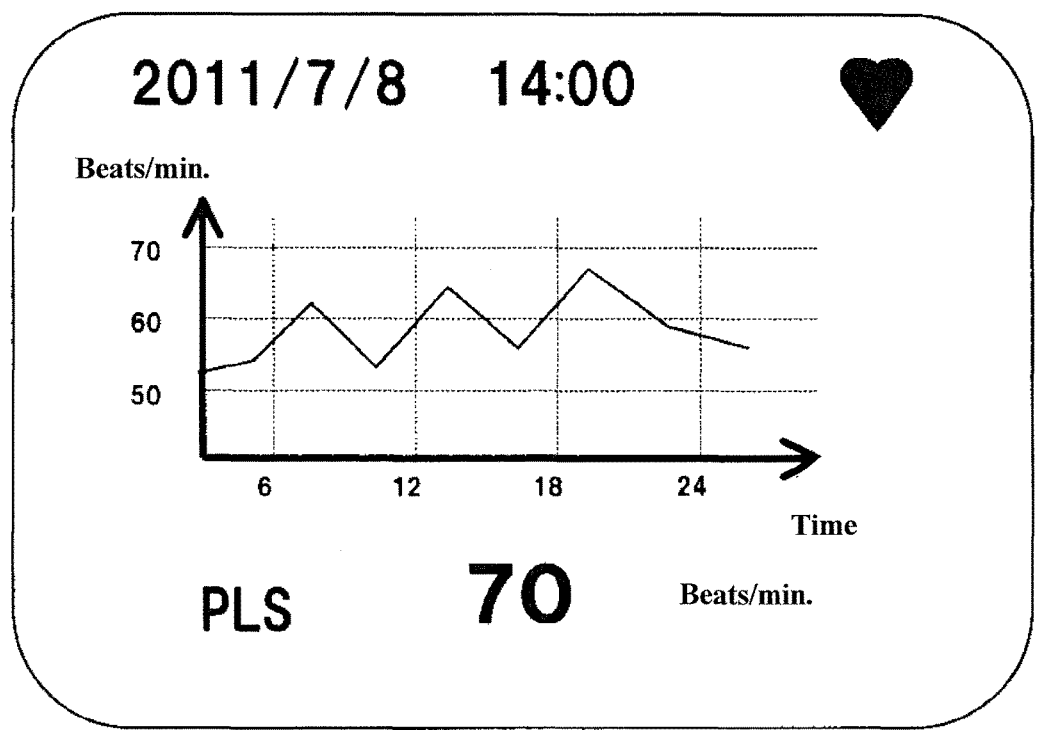
FIG. 11 is a diagram illustrating a specific example of a display screen during the pulse measurement operation.

Note that, during the time the pulse measurement operation is repeatedly being performed, without the blood pressure measurement operation being performed, according to one or more embodiments of the present invention, the CPU 40 displays a screen to that effect on display unit 4, such as that illustrated in FIG. 11. By doing so in this way, the patient and the person measuring can see that the sphygmomanometer 1 is in the pulse measurement operation. Note that, at this time, as illustrated in FIG. 11, the results of the repeatedly performed pulse measurements may be displayed together in sequence with the measurement results of the pulse rate at the time of display.

In the case that pulse rate is not calculated through the pulse measurement operation when the count of the continued measurement of elapsed time is 2 minutes or more, that is, in the case where pulse is not calculated for 2 minutes or more (YES at step S125), the CPU 40, at step S127, displays a pulse measurement error on display unit 4 and leaves a flag in the memory 7 at step S129.

In the case where pulse is not calculated in 2 minutes or more (YES at steps S125 and S129) and also when the power switch is pressed (YES at step S113), the CPU 40, at step S115, completely opens the valve 22 and completes the operation. By doing so, the air inside the air bladder for light compression 8 is emitted and the operation completes.

Figure 12:
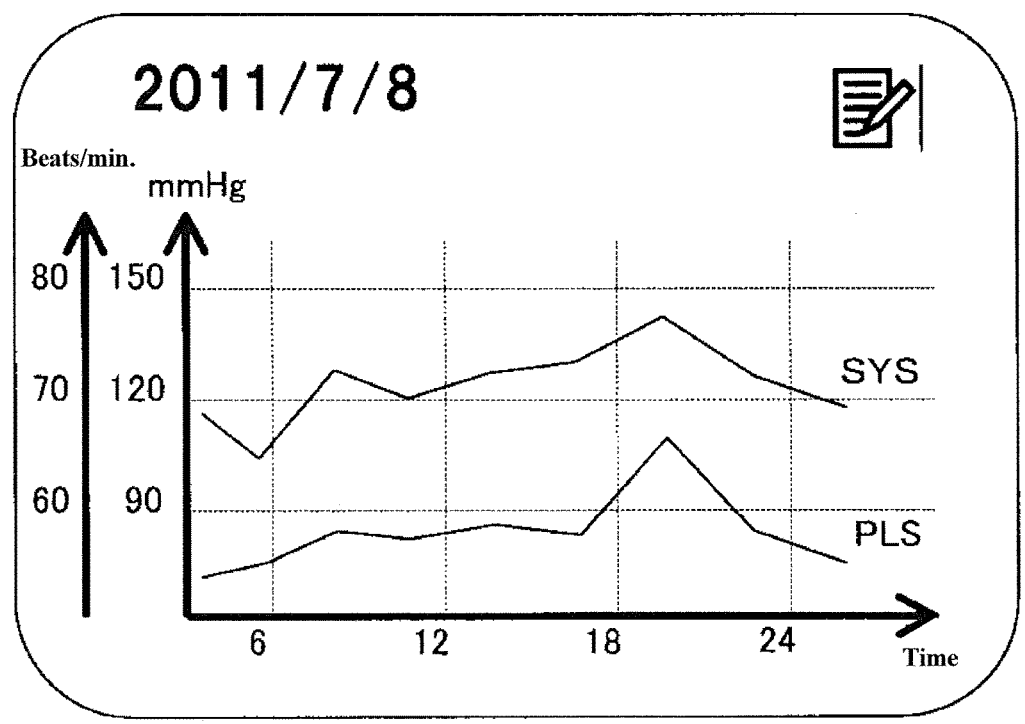
FIG. 12 is a diagram illustrating a specific example of a display screen after the pulse measurement operation.

After a series of operations completes, measurement results like those illustrated in FIG. 12 may be displayed. At this time, in the case where a measurement operation of a prescribed period of time is performed, the measurement results of the mechanism, in other words, the various measurement results in the case where blood pressure measurement operations and pulse measurement operations are performed a plurality of times, may be displayed in sequence, as illustrated in FIG. 12. As such, changes during the period of time can be known.

Effect of the Embodiments

With a sphygmomanometer 1 configured in this way and by operating as aforementioned in timing other than that of a blood pressure measurement operation, a pulse is measured in that period where a narrow extent of above a radial artery of a wrist, which is a measurement location, is lightly compressed by an air bladder 8 that is smaller than an air bladder 13 for measuring blood pressure and a sensor for detecting a pulse wave is pressed on the measurement location. Because of this, blood stasis of the wrist can be suppressed and pulse can be measured accurately over a long period of time.

Other Examples

Note that, a photoelectronic sensor is used for pulse wave detection in the above example, but pulse wave detection is not limited to photoelectronic sensors. As other examples, a pulse wave may be detected by detecting a pressure variation in conjunction with an artery volume change superimposed on an inner pressure change of an air bladder for light compression 8 and an impedance sensor may also be used.

Also, in the example above, an example is illustrated where one photoelectronic sensor having one set of a light emitting element and a light receiving element is used for pulse wave detection, but two or more photoelectronic sensors may be used. Also, as aforementioned, in the case where an impedance sensor is used, two or more impedance sensors may be used.

Figure 13:
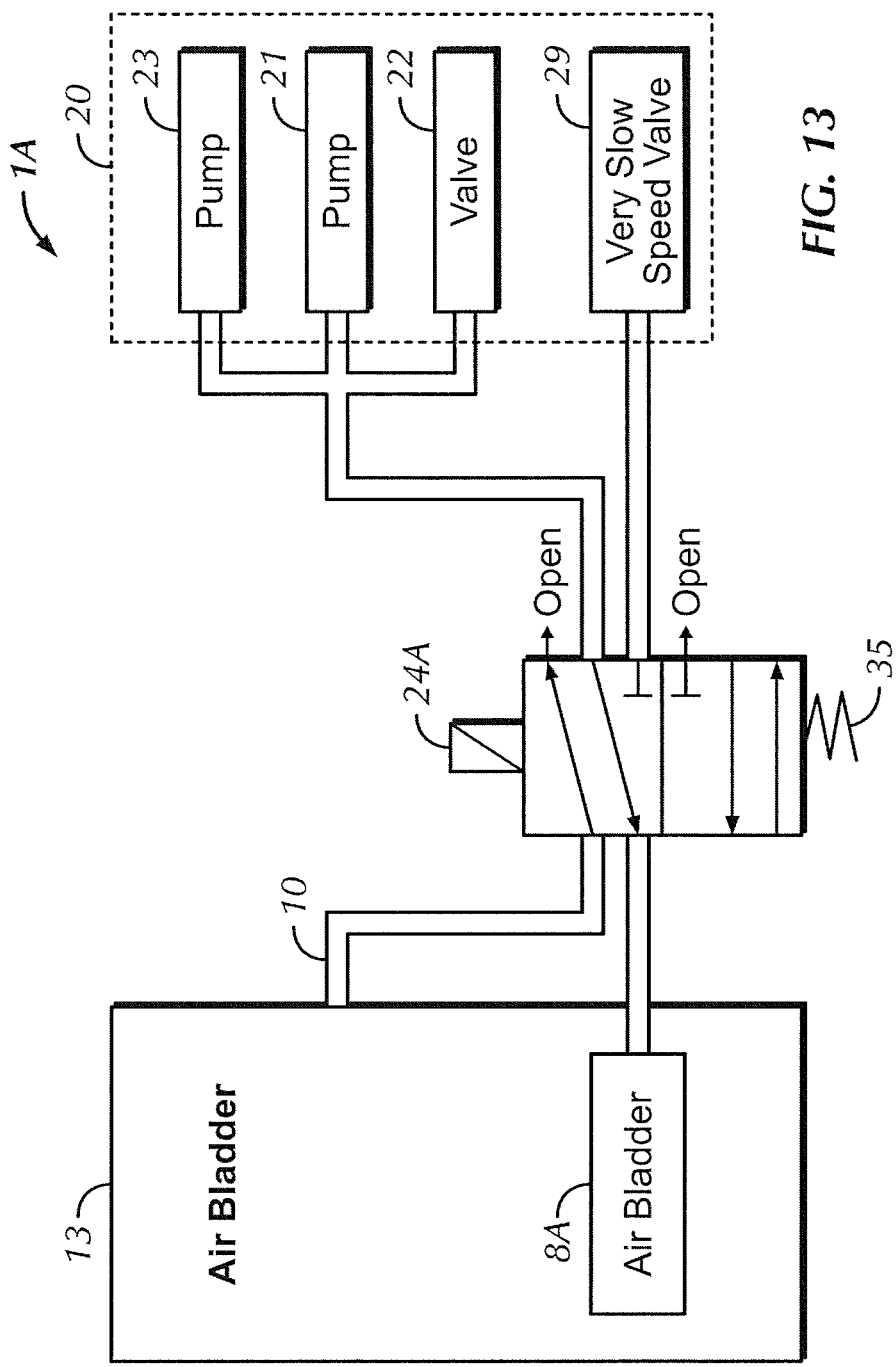
FIG. 13 is a diagram illustrating a specific example of another configuration about a configuration portion related to an inner pressure control of the sphygmomanometer.

FIG. 13 is a diagram illustrating a specific example of a configuration about a configuration portion related to an inner pressure control of a sphygmomanometer 1A using an air bladder for pulse detection.

With reference to FIG. 13, in this case, an air bladder for pulse wave detection 8A is provided instead of the air bladder for light compression 8 and a 5-port valve 24A and a switching device 35 therefor are used as a switching valve 24 for an air system 20. Also, a very slow speed valve 29 is included in air system 20.

The switching device 35 is connected to a CPU 40 not illustrated in FIG. 13 and follows a control signal therefrom to switch the connection of air bladders 8A and 13 to the air system 20 with the 5-port valve 24A.

Specifically, a connected state at a time of measuring pulse is as illustrated in FIG. 13. That is, at the time of measuring pulse, an air bladder 13 is opened and the air bladder 8A is connected to the air system 20. Also, the very slow speed valve 29 of the air system 20 is in a state of not being connected. Through this, the air inside air bladder 13 is emitted and the inner pressure of the air bladder 8A is controlled through the air system 20.

Figure 14:
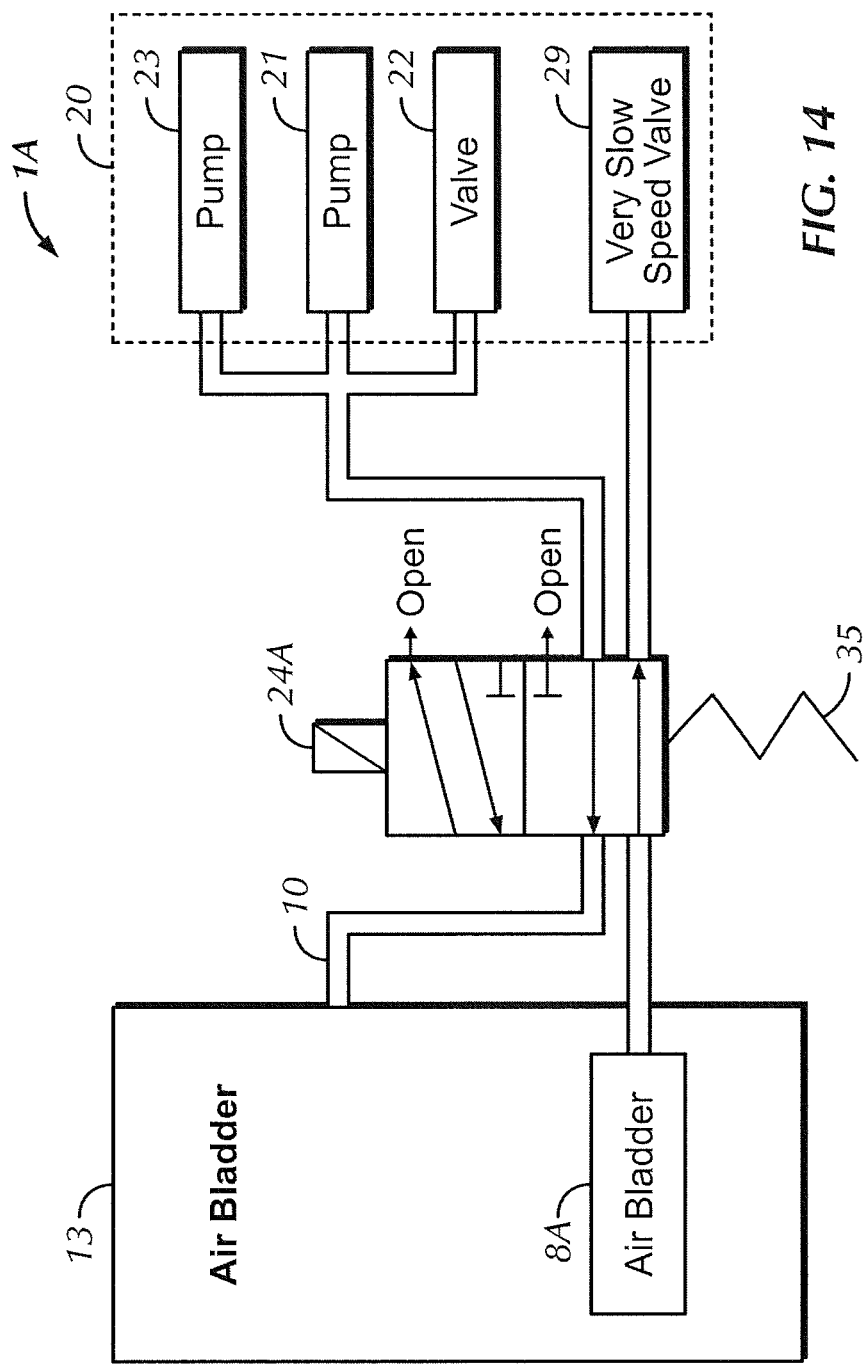
FIG. 14 is a figure indicating a connected state at the time of measuring blood pressure.

A connected state at a time of measuring blood pressure is as illustrated in FIG. 14. That is, at the time of measuring blood pressure, the air bladder 13 is connected to the air system 20, and the air bladder 8A is connected to the very slow speed valve 29. Through this, the inner pressure of the air bladder 13 is controlled through air system 20, and the air inside the air bladder 8 is gradually emitted from the very slow speed valve 29.

Figure 15:
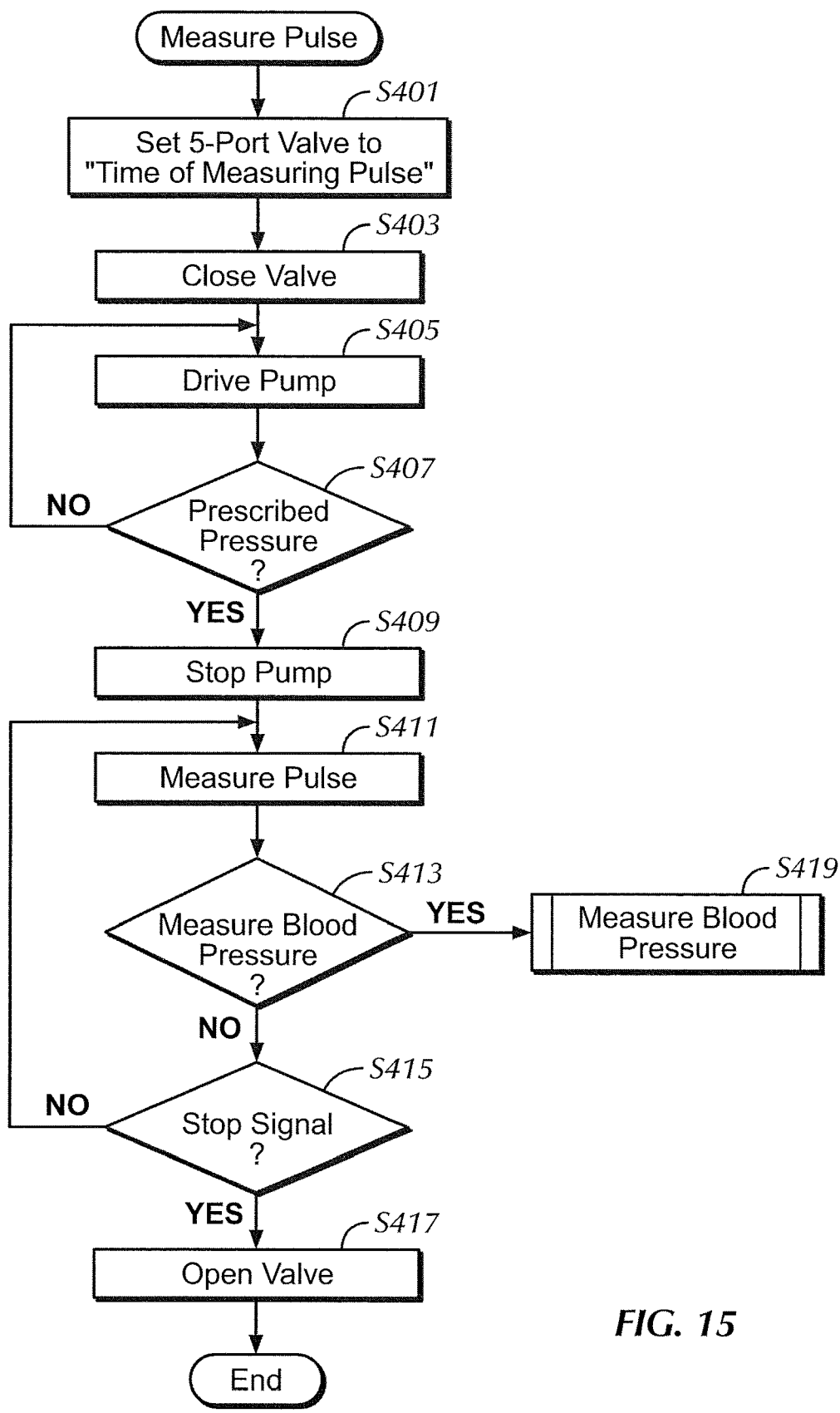
FIG. 15 is a flowchart indicating another example of the pulse measurement operation.
Figure 16:
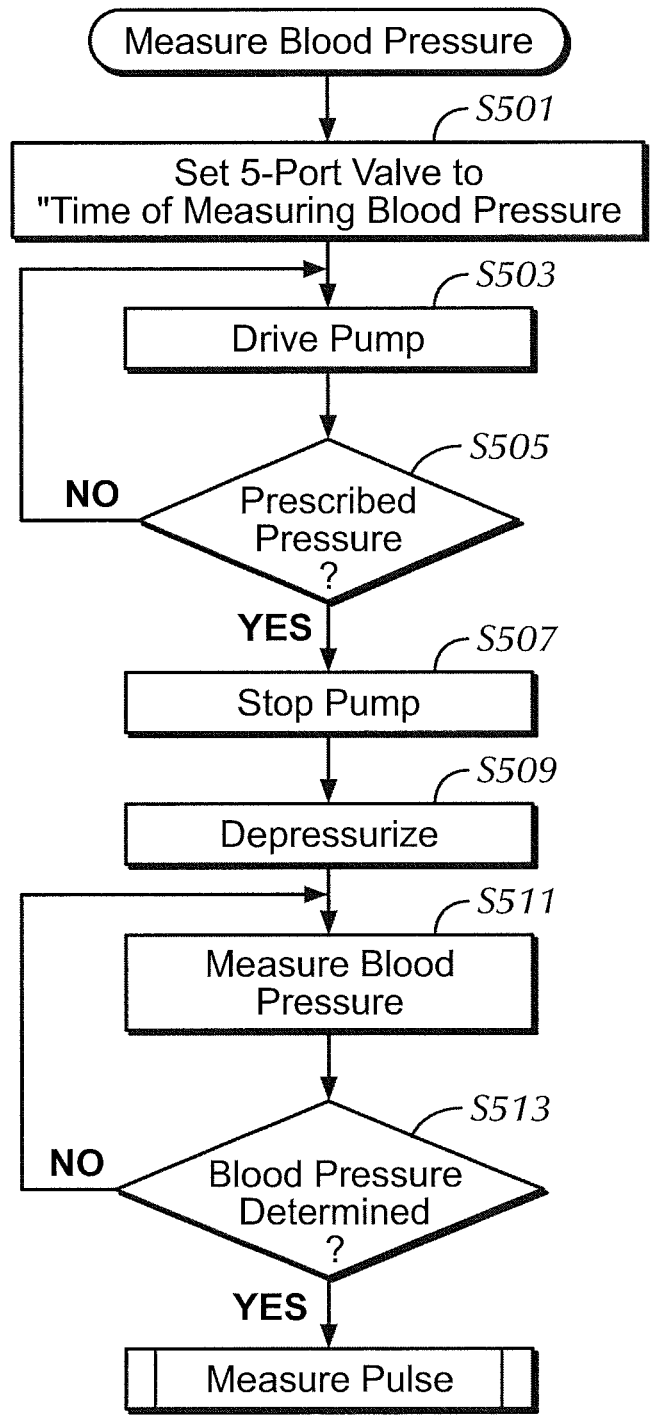
FIG. 16 is a flowchart indicating another example of the blood pressure measurement operation.

FIG. 15 and FIG. 16 are flowcharts indicating the operation in the sphygmomanometer 1A at this time. FIG. 15 indicates the pulse measurement operation and FIG. 16 indicates the blood pressure measurement operation.

That is, with reference to FIG. 15, the CPU 40, upon putting the 5-port valve 24A in a connected state of the time of measuring pulse at step S401, as illustrated in FIG. 13, closes a valve 22 at step S403. Then, at step S405, drives a pump 21 and pressurizes the air bladder 8A until the air bladder 8A is at a prescribed pressure. When the above prescribed pressure is reached (YES at step S407), the CPU 40, at step S409, stops the driving of the pump 21 and maintains the prescribed pressure. Then, the CPU 40 measures pulse at step S411. After that, the CPU 40 monitors an instruction input to perform blood pressure measurement and, in the case where there is no such input (NO at step S413), the CPU 40 monitors an instruction input of a stop signal and continues the aforementioned pulse measurement until the instruction input of the stop signal is made (NO at step S415).

Then, when the instruction input of the stop signal is made (YES at step S415), the CPU 40 opens the valve 22 at step S417 and completes the single series of operations. Through this, the air inside the air bladder 8A is emitted and the measurement operation completes.

On the other hand, in the case that the instruction input to perform blood pressure measurement is made (YES at step S413), the CPU 40 executes the blood pressure measurement operation (step S419).

Specifically, with reference to FIG. 16, the CPU 40, upon putting the 5-port valve 24A in a connected state of the time of measuring blood pressure in step S501, as illustrated in FIG. 14, drives the pump 21 and pressurizes the air bladder 13 until the air bladder 13 is at a prescribed pressure at step S503. When the above prescribed pressure is reached (YES at step S505), the CPU_40, at step S507, stops the driving of the pump 21 and gradually opens the valve 22 at step S509. Through this, the air bladder 13 is depressurized. The CPU 40, at step S511, performs the blood pressure measurement through a decompression process. The blood pressure measurement of step S511 is performed until blood pressure is determined (NO at step S513). The CPU 40 completes the blood pressure measurement operation when blood pressure is determined (YES at step S513) and returns to the pulse measurement operation of FIG. 15.

FIG. 17 is a figure that indicates a change in inner pressure of the air bladder 8A (an air bladder for pulse measurement) when performing the blood pressure measurement operation during the pulse measurement operation and then returning to the pulse measurement operation (A) and a change in inner pressure of the air bladder 13 (the air bladder for blood pressure measurement) (B).

Figure 17A:
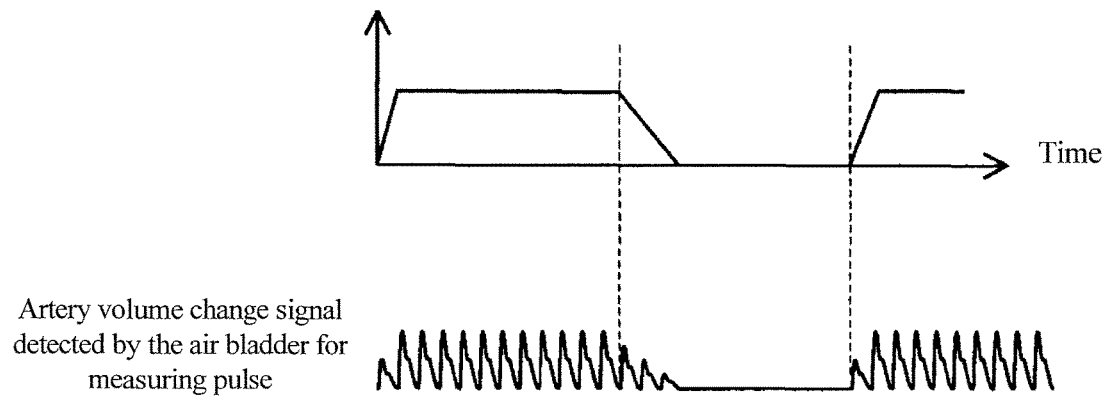
FIG. 17A indicates a change in inner pressure of an air bladder for pulse measurement when performing the blood pressure measurement operation during the pulse measurement operation and then returning to the pulse measurement operation and FIG. 17B indicates a change in inner pressure of an air bladder for blood pressure measurement.

With reference to FIG. 17(A), during the pulse measurement operation, the air bladder 8A being generally maintained at a fixed pressure, a pulse wave is detected as a pressure variation in conjunction with an artery volume change superimposed on that pressure change. Because the inner pressure of the air bladder 8A is gradually depressurized through the very slow speed valve 29 at the time of moving from the pulse measurement operation to the blood pressure measurement operation, effects on the blood pressure measurement operation during that period can be suppressed.

Figure 17B:
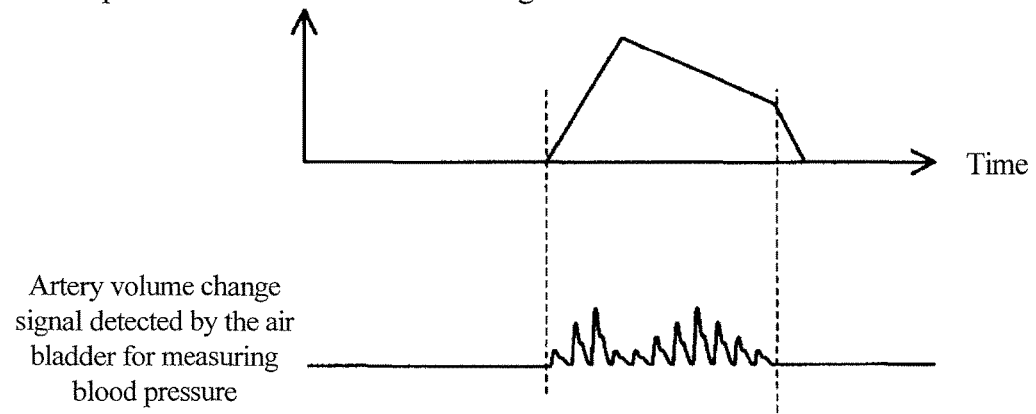

With reference to FIG. 17(B), the air bladder 13, having no inner pressure compressing the measurement location during the pulse measurement operation, pressurizes and depressurizes as aforementioned during the blood pressure measurement operation. At the same time as blood pressure value is calculated based on a pressure variation in conjunction with a change in artery volume superimposed on a pressure change during that period, pulse is also measured.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A blood pressure and pulse measurement device comprising:
    a cuff comprising a first air bladder for wrapping around a measurement location of a patient, wherein the first air bladder is an air bladder for measuring;
    a pressure sensor connected to the cuff that measures an inner pressure of the first air bladder;
    a pressing member mounted on a portion of an inner face of the first air bladder for contacting the measurement location of the patient when the cuff is wrapped therearound;
    a pulse wave sensor mounted on the pressing member for detecting a pulse of the patient; and
    a CPU that receives instructions via an operation unit to cause the device to measure a blood pressure and pulse, wherein when a measuring routine is activated, and the CPU receives instructions to measure the blood pressure, the first air bladder of the cuff is inflated to increase the inner pressure to a sufficient level such that the blood pressure of the patient can be measured by the pressure sensor, and then the first air bladder of the cuff is deflated,
    wherein at a time of measuring blood pressure, only the first air bladder pressurizes,
    wherein when the measuring routine is activated, and the CPU does not receive instructions to measure the blood pressure, air of the first air bladder of the cuff is released such that the measurement location of the patient is not substantially pressed by the first air bladder, and, while the first air bladder of the cuff is not pressurized, the measurement location of the patient is pressed by the pressing member with sufficient pressure such that the pulse of the patient can be detected by the pulse wave sensor at a position where the measurement location of the patient is contacted by the pulse wave sensor, and
    wherein at a time of measuring pulse, only the pressing member pressurizes.

2. The device according to claim 1, wherein the pulse wave sensor is mounted on the pressing member at a position where the pressing member contacts the measurement location.

3. The device according to claim 1, wherein the pressing member is constituted such that the pulse wave sensor is positioned above an artery of the patient.

4. The device according to claim 1, wherein the pressing member comprises a second air bladder, and at the time of measuring blood pressure, air of the second air bladder is released such that the measurement location of the patient is substantially pressed only by the first air bladder.

5. The device according to claim 1, wherein the pulse wave sensor is a photoelectronic sensor.

6. The device according to claim 1, wherein the pulse wave sensor is an impedance sensor.

7. The device according to claim 1, wherein the cuff and the pressing member are constituted such that the cuff and the pressing member can be mounted on a wrist of the patient.

8. The device according to claim 1, wherein measurement of blood pressure is instructed by the operation unit at a predetermined interval.

9. The device according to claim 1, wherein detection of the pulse of the patient is suspended when the first air bladder is inflated and/or deflated for measurement of blood pressure.

10. A cuff of a blood pressure and pulse measurement device comprising:
    a first air bladder for wrapping around a measurement location of a patient;
    a pressure sensor connected to the first air bladder that measures an inner pressure of the first air bladder;
    a pressing member mounted on a portion of an inner face of the first air bladder, which contacts the measurement location of the patient when the cuff is wrapped therearound;
    a pulse wave sensor mounted on the pressing member for detecting pulse of the patient; and
    a CPU provided in the blood pressure pulse and measurement device and connected to the cuff that receives instructions via an operation unit to cause the device to measure a blood pressure and pulse of the patient,
    wherein when a measuring routine is activated, and the CPU receives instructions to measure the blood pressure, the first air bladder of the cuff is inflated to increase inner pressure to a sufficient level such that the blood pressure of the patient can be measured by the pressure sensor and then deflated, and wherein when the measuring routine is activated, and the CPU does not receive instructions to measure the blood pressure, air of the first air bladder of the cuff is released such that the measurement location of the patient is not substantially pressed by the cuff, and, while the first air bladder of the cuff is not pressurized, the measurement location of the patient is pressed by the pressing member with sufficient pressure such that a pulse of the patient can be detected by the pulse wave sensor at a position where the measurement location of the patient is contacted by the pulse wave sensor.

11. A method for measuring a blood pressure and a pulse of a patient comprising:

wrapping a cuff comprising a first air bladder and a pressure sensor around a measurement location of the patient, wherein the cuff is provided with a pressing member mounted on a portion of an inner face of the first air bladder and a pulse wave sensor mounted on the pressing member;

inflating the first air bladder of the cuff to a sufficient inner pressure level such that the blood pressure of the patient can be detected by the pressure sensor, and then deflating the first air bladder of the cuff, and at a time of measuring a pulse, releasing air of the first air bladder of the cuff such that measurement location of the patient is not substantially pressed by the first air bladder, and, while the first air bladder of the cuff is not pressurized, the measurement location is pressed by the pressing member with sufficient pressure such that a pulse of the patient can be detected by the pulse wave sensor at a position where the pulse wave sensor contacts the measurement location of the patient.

12. The method according to claim 11, wherein the pulse wave sensor is mounted on the pressing member at a position where the pressing member contacts the measurement location.

13. The method according to claim 11, wherein the pressing member is constituted such that the pulse wave sensor is positioned above an artery of the patient.

14. The method according to claim 11, wherein the pressing member comprises a second air bladder, and at a time of measuring blood pressure, air of the second air bladder is released such that the measurement location of the patient is substantially pressed only by the first air bladder.

15. The method according to claim 11, wherein the pulse wave sensor is a photoelectronic sensor.

16. The method according to claim 11, wherein the pulse wave sensor is an impedance sensor.

17. The method according to claim 11, wherein the cuff and the pressing member are constituted such that the cuff and the pressing member can be mounted on a wrist of the patient.

18. The method according to claim 11, wherein measurement of blood pressure is instructed by the operation unit at a predetermined interval.

19. The method according to claim 11, wherein detection of the pulse of the patient is suspended when the first air bladder is inflated and/or deflated for measurement of blood pressure.

* * * * *